United States Patent [19]

Bailey et al.

[11] Patent Number: 4,720,574

[45] Date of Patent: Jan. 19, 1988

[54] ANTIMICROBIAL COMPOUND BIS (CARBOMETHOXYMETHYL) ADIPATE

[75] Inventors: August V. Bailey, New Orleans; Gordon J. Boudreaux, Metairie; Gene Sumrell, New Orleans, all of La.

[73] Assignee: The United States of America as represented by the Secretary of Agriculture, Washington, D.C.

[21] Appl. No.: 673,299

[22] Filed: Nov. 20, 1984

Related U.S. Application Data

[60] Continuation of Ser. No. 308,743, Oct. 5, 1981, abandoned, which is a division of Ser. No. 235,812, Feb. 19, 1981, Pat. No. 4,346,043.

[51] Int. Cl.$^4$ .................... C07C 69/675; C07C 69/44
[52] U.S. Cl. ................................. 560/185; 560/190; 562/579; 562/590

[58] Field of Search ............... 424/313; 560/190, 185; 514/547

[56] References Cited

U.S. PATENT DOCUMENTS 2,608,577  8/1952  Weesner .............................. 560/185
3,098,867  7/1963  Marvel et al. ....................... 560/190
3,567,749  3/1971  Neugebauer et al. .............. 560/190

Primary Examiner—Werren B. Lone
Assistant Examiner—Vera C. Clarke
Attorney, Agent, or Firm—M. Howard Silverstein; David G. McConnell; Raymond C. Von Bodungen

[57] ABSTRACT

The antimicrobial compound, bis(carbomethoxymethyl) adipate is disclosed. It was prepared by condensing the methyl ester of glycolic acid and the acid chloride of adipic acid. Tests for antimicrobial activity exhibit potent antimicrobial activity against molds, yeasts, and gram-positive and gram-negative bacteria.

1 Claim, No Drawings

ANTIMICROBIAL COMPOUND BIS (CARBOMETHOXYMETHYL) ADIPATE

CROSS REFERENCE TO RELATED APPLICATIONS

This is a continuation of application Ser. No. 308,743, filed Oct. 5, 1981 now abandoned which was a division of application Ser. No. 235,812, filed Feb. 19, 1981, which issued on Aug. 24, 1982 as U.S. Pat. No. 4,346,043.

BACKGROUND OF THE INVENTION

1. Field of the Invention

This invention concerns antimicrobial compounds.

2. Description of the Prior Art

The germicidal activity of certain lipid compounds has long been known. Soap is a familiar example. Various fatty acids and their derivatives have found use as antiseptics and disinfectants, and also as preservatives for drugs and cosmetics. In recent times, however, the fatty antimicrobials have, to a considerable degree, been replaced for such applications by more potent synthetic non-fatty compounds. More recently, many of the latter materials have come under suspicion by regulatory agencies because of their toxicity and side reactions. The pendulum is swinging back in favor of naturally occurring or derived lipid materials for application as antimicrobials and preservatives in food, pharmaceuticals, and other organic materials of commerce which are subject to bacterial or fungal attack, and in the formulation of self-preserving cosmetics.

In the search for antimicrobial agents for use in commercial products, it is necessary to ascertain the relative degree of inhibition that can be attained with any specific microorganisms under normal conditions of product use in accordance with the chemical and physical properties of the product. Minor differences in structure may result in one compound being inactive while a very similar compound has potent broad spectrum antimicrobial activity. Also, some compounds may be selectively active against one or a small number of microorganisms, while another very similar compound shows a broad spectrum of activity against many types of organisms. Thus, screening is necessary in evaluating new compounds for potential use as antimicrobial agents, followed by intensive testing for specific end uses of those compounds found to have microbial activity.

SUMMARY OF THE INVENTION

This invention involves the preparation of the new glycolic acid derivative, bis(carbomethoxymethyl)adipate:

which has potent broad spectrum antimicrobial activity. It is very effective against a wide variety of microorganisms that include bacteria, yeasts, and molds, and is extremely useful as an additive in food and other commercial products.

DESCRIPTION OF THE PREFERRED EMBODIMENTS

The compound which is the subject of this invention is a glycolic acid derivative which is substituted at the hydroxy and carboxyl functions and has the following structure:

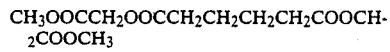

This compound was prepared by the condensation of the methyl ester of glycolic acid with the acid chloride of adipic acid.

The bioactivity of this compound has been established by applicants in vitro but, as will be apparent to those skilled in the arts pertaining to the growth inhibition of bacteria, yeasts, and molds, the compound, besides being used as such, will for utilitarian purposes commonly be formulated using a diluent that can be either liquid, viscous, or solid.

A wide variety of extending agents is operable, the only significant requirement being that the diluent or extender be inert with respect to the compound involved. Petroleum jellies, various alcohols and polyols, vegetable oils and the like are suitable.

Difco Bacto dehydrated nutrient agar at pH 6.8, Difco Bacto dehydrated yeast mycological agar at pH 4.5, and Difco dehydrated mycological agar at pH 7.0 were used to test inhibition of the bacteria, yeast, and mold cultures, respectively. The microorganisms used were obtained from stock cultures. After the cultures were incubated for 48 hours at room temperature, suspensions of the microorganisms were prepared. One loop ($\frac{1}{4}$ inch) of spores of sporeformers was removed from the cultures and placed in 5 ml sterile 0.5% saline solution. With nonspore formers, one loop of vegetative cells was suspended in 5 ml sterile 0.5% saline solution. The suspension served as the inoculum for the estimation of activity against microbial growth.

Hardened agar plates were inoculated by placing 3 drops of the suspension on the agar. Microorganisms were spread over the surface of the plates with sterile glass rods. These plates were employed in the activity estimation against microbial growth. Paper discs 6.5 mm in diameter, made from Whatman No. 1 filter paper, were used in the evaluation of the liquid compounds, and stainless steel cylinders of 5 mm inside diameter were used for the solid compounds. The paper discs, completely saturated with the liquid test compound, were placed on the surface of agar plates inoculated with test organisms. Solid compounds were placed in stainless steel cylinders in direct contact with the inoculated plates. No carrier solvent was employed. To eliminate any errors which could result from an insufficient number of tests, a minimum of three experiments, at different times, employing duplicate plates were made for each compound under test. All plates were incubated at the optimum growing temperature for each organism and readings were taken after 24, 48, 72 and 120 hour periods.

The organisms used in the tests were: a gram-positive bacterium, *Staphylococcus aureus;* a gram-negative bacterium, *Escherichia coli;* a yeast, *Candida utilis;* and a mold, Penicillium species. The data from tests on bis(carbomethoxymethyl) adipate and some related derivatives of glycolic acid are tabulated in Table I. It will be noted that, while all of these glycolic acid derivatives possess some antimicrobial activity, and some are potent against one or more of the microorganisms, bis(carbomethoxymethyl) adipate has broad spectrum activity being very potent against all of the organisms used in the tests.

The preparation of bis(carbomethoxymethyl) adipate is given in Example 1.

EXAMPLE 1 bis(Carbomethoxymethyl) adipate 36.6 g (0.2 mole) of adipoyl chloride was added to a stirred solution of 36 g (0.4 mole) of methyl glycolate in 40 ml of pyridine. The precipitated pyridine hydrochloride was filtered, washed with benzene, and discarded. The benzene solution of bis(carbomethoxymethyl) adipate was water washed, dried over sodium sulfate, and the solvent stripped off using a rotary evaporator. The yield of product was essentially quantitative. Its structure was established by infrared and nuclear magnetic resonance spectroscopy. It had $n_D^{30}$ 1.4445 and $d_4^{30}$ 1.1961.

EXAMPLE 2 bis(Carbobutoxymethyl) adipate This compound was prepared from 52.8 g (0.4 mole) of n-butyl glycolate and 36.6 g (0.2 mole) of adipoyl chloride by the procedure of Example 1. Its structure was established by infrared and nuclear resonance spectroscopy. It had $n_D^{25}$ 1.4461 and $d_4^{25}$ 1.0840.

TABLE I

ANTIMICROBIAL ACTIVITY OF GLYCOLIC ACID DERIVATIVES

| No. | Compound | Antimicrobial activity[a] microorganisms[b] | | | |
|-----|----------|---|---|---|---|
| | | A | B | C | D |
| 1 | N,N—bis(Pelargonoyloxyethyl)pelargonoyloxyacetamide | oo | oo | + | oo |
| 2 | N,N—bis(Lauroyloxyethyl)lauroyloxyacetamide | o | o | oo | oo |
| 3 | N,N—bis(Oleoyloxyethyl)oleoyloxyacetamide | o | o | o | o |
| 4 | N,N—bis(Trimethylacetyloxyethyl)trimethylacetyloxyacetamide | + | o | ++ | + |
| 5 | Carboethoxymethyl hydrocinnamate | oo | oo | + | oo |
| 6 | bis(Carbomethoxymethyl) adipate | + | + | ++ | ++ |

[a] ++ = Zone of inhibition at least 0.5 cm beyond disc or cylinder area at 120 hr.
+ = Zone of inhibition less than 0.5 cm beyond disc or cylinder area at 120 hr.
oo = Organism failed to grow on disc or cylinder area at 120 hr.
o = Slight growth on the disc or cylinder area at 120 hr.
[b] A = *Staphylococcus aureus.*
B = *Escherichia coli.*
C = *Candida utilis.*
D = *Penecillium species.*

We claim:

1. The antimicrobially active compound bis(carbomethoxymethyl) adipate:

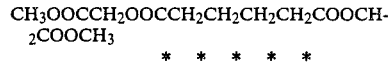

CH₃OOCCH₂OOCCH₂CH₂CH₂CH₂COOCH₂COOCH₃

* * * * *